United States Patent [19]

Badone et al.

[11] Patent Number: 5,449,813
[45] Date of Patent: Sep. 12, 1995

[54] NEW PHENYLETHANOLAMINO- AND PHENYLETHANOLAMINOMETHYL-TETRALINES, PROCESS FOR THE PREPARATION THEREOF, INTERMEDIATES IN SAID PROCESS AND PHARMACEUTICAL COMPOSITIONS CONTAINING THEM

[75] Inventors: Domenico Badone, Induno Olona; Umberto Guzzi, Milan; Roberto Cecchi, Lodi Milano, all of Italy

[73] Assignee: Sanofi, Paris, France

[21] Appl. No.: 358,380

[22] Filed: Dec. 19, 1994

Related U.S. Application Data

[63] Continuation of Ser. No. 12,388, Feb. 2, 1993, Pat. No. 5,401,879, which is a continuation of Ser. No. 836,253, Feb. 18, 1992, Pat. No. 5,210,276.

[30] Foreign Application Priority Data

Feb. 18, 1991 [EP] European Pat. Off. ............ 91400415

[51] Int. Cl.⁶ ........................................... C07C 229/42
[52] U.S. Cl. .................................................... 560/19
[58] Field of Search ........................................ 560/19

[56] References Cited

U.S. PATENT DOCUMENTS 5,206,418 4/1993 Nakai et al. ..................... 560/139
5,206,428 4/1993 Nakai et al. ..................... 562/427

Primary Examiner—José G. Dees
Assistant Examiner—Samuel Barts
Attorney, Agent, or Firm—Bacon & Thomas

[57] ABSTRACT

Phenylethanolamino- and phenylethanolaminomethyl-tetralines of formula (I)

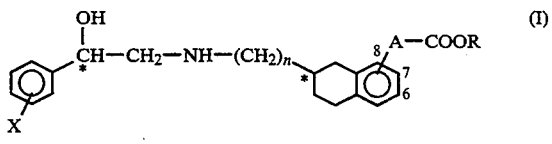

wherein
X represents a hydrogen atom, a halogen atom, a ($C_1$-$C_4$)alkyl group or a trifluoromethyl group,
A represents a bond between the —COOR group and the tetraline ring, a ($C_1$-$C_4$)alkylene or a ($C_2$-$C_4$)alkenylene group,
R is hydrogen or a ($C_1$-$C_4$)alkyl group, and
n is 0 or 1
and their salts, are typically prepared by reaction of an epoxide of formula (IIa)

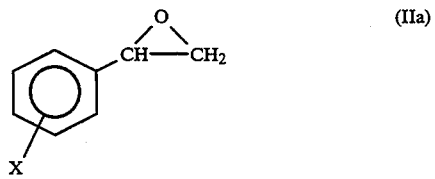

with a tetraline derivative of formula (III)

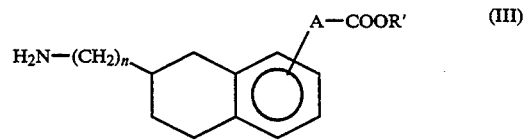

wherein A and n are as defined above and R' is a ($C_1$-$C_4$)alkyl group, optionally followed by basic hydrolysis to obtain the compounds (I) wherein R is hydrogen. The new compounds show very interesting properties as antidepressant and intestinal spasmolytic agents. The new intermediates of formula (III) are also claimed.

6 Claims, No Drawings

NEW PHENYLETHANOLAMINO- AND PHENYLETHANOLAMINOMETHYL-TETRALINES, PROCESS FOR THE PREPARATION THEREOF, INTERMEDIATES IN SAID PROCESS AND PHARMACEUTICAL COMPOSITIONS CONTAINING THEM

This application is a continuation of application Ser. No. 08/012,388, filed Feb. 2, 1993, now U.S. Pat No. 5,401,879, which is a continuation application of Ser. No. 07/836,253, filed Feb. 18, 1992, now U.S. Pat. No. 5,210,276.

The present invention concerns new phenylethanolamino- and phenylethanolaminomethyl-tetralines, the process for the preparation thereof, the key intermediates in said process and the pharmaceutical compositions containing them.

Phenylethanolamino- and phenylethanolaminomethyl-tetraline derivatives characterised by the presence of an oxygen atom linked to the tetraline ring have been described as lipolytic and intestinal motility modulating agents in EP-A-211,721, EP-A-383,686, and EP-A-436,435.

It has now been found that phenylethanolamino- and phenylethanolaminomethyl-tetralines bearing a carboxy or alkoxycarbonyl group linked to the 1,2,3,4-tetrahydronaphthalene ring either directly or through a lower alkylene or alkenylene group have very interesting pharmacological properties as antidepressant agents. Accordingly, in one of its embodiments, the present invention relates to compounds of formula (I)

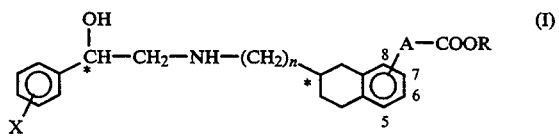

wherein
X represents a hydrogen atom, a halogen atom, a ($C_1$–$C_4$)alkyl or a trifluoromethyl group,
A represents a bond between the —COOR group and the tetralin nucleus, a ($C_1$–$C_4$)alkylene or a ($C_2$–$C_4$)alkenylene radical,
R represents a hydrogen atom or a ($C_1$–$C_4$)alkyl, and n is 0 or 1,
and their salts.

In the present application the terms "($C_1$–$C_4$)alkyl" and "($C_1$–$C_4$)alkylene" designate mono- or di-valent radicals, respectively, of straight or branched saturated hydrocarbons which may contain from 1 to 4 carbon atom. Preferably, the term "($C_1$–$C_4$)alkyl" designates methyl or ethyl, while the term "($C_1$–$C_4$)alkylene" preferably indicates a methylene, ethylene or propylene radical which may optionally be methyl-substituted.

The term "($C_2$–$C_4$)alkenylene" identifies a divalent radical of a straight or branched hydrocarbon containing from 2 to 4 carbon atoms and a double bond.

Preferably the term "($C_2$–$C_4$)alkenylene" represents a vinylene or 1,3-propylene radical.

The term "halogen" comprises the four halogens: fluoro, chloro, bromo and iodo, chloro being preferred.

The term "tetraline" is an abbreviation for 1,2,3,4-tetrahydronaphthalene.

Salts of the compounds of formula (I) according to the present invention include the addition salts with pharmaceutically acceptable mineral or organic acids such as the hydrochloride, hydrobromide, sulfate, hydrogensulfate, dihydrogenphosphate, citrate, maleate, tartrate, fumarate, gluconate, methanesulfonate, 2-naphthalenesulfonate, etc. as well as the addition salts which allow an easy separation or crystallisation of the compounds of formula (I), such as the picrate, the oxalate or the addition salts with optically active acids, such as camphorsulfonic, mandelic, or substituted mandelic acids.

Furthermore when the compounds of formula (I) have a free carboxy group (R=H) the salts include also the salts with mineral bases, preferably those with alkali metals such as sodium or potassium or with organic bases such as trometamol.

In the above formula (I) the two asymmetric carbon atoms are marked by asterisks. The compounds of formula (I) may therefore exist as at least four different stereoisomers, (R,R), (R,S), (S,S), and (S,R). The optically pure isomers as well as any mixture of two, three, or all four isomers, in any proportion thereof, do fall within the scope of the present invention. Other chiral centres may be present in the radical A. Analogously the stereoisomers deriving from the presence of an additional chiral centre and their mixtures are part of the present invention. For the expression of pharmacological activity, the preferred configuration of the ethanolamino chain chiral carbon is absolute configuration R.

A preferred group of compounds of the present invention comprises those compounds of formula (I) wherein X represents a hydrogen atom or a 3-positioned halogen atom or trifluoromethyl group, and the —A—COOR group is linked to position 6 or 7 of tetraline ring, and salts thereof.

A other preferred group of compounds comprises those compounds of formula (I) wherein the —A—COOR group is linked to position 6 or 7 of the tetraline ring and A represents a bond between the —COOR group and the tetraline ring, an alkylene of 1 or 2 carbon atoms, or an alkenylene of 2 carbon atoms, and salts thereof.

Particularly advantageous compounds of the present invention are the compounds of formula (I) wherein X is a 3-positioned halogen atom, the —A—COOR group is at position 6 or 7 of the tetraline ring and A represents a bond between the —COOR group and the tetraline ring, or an alkylene of 1 or 2 carbon atoms, and R represents hydrogen, methyl or ethyl, and salts thereof.

The compounds of formula (I) may be prepared by a process characterised in that a compound of formula (II)

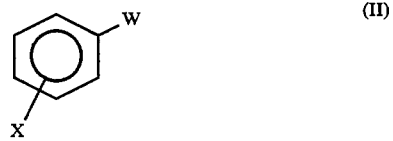

wherein X is as defined above and —W represents one of the following groups:

-continued

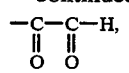   (b)

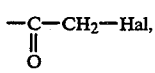   (c)

or

   (d)

wherein Hal stands for chloro, bromo, or iodo and Y represents a —COOH group or a functional derivative thereof, is reacted with a compound of formula (III)

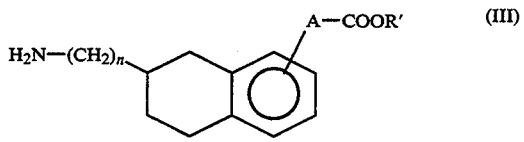   (III)

wherein A and n are as defined above and R' is ($C_1$-$C_4$)alkyl and, when —W is different from (a), treating the thus obtained product with a suitable reducing agent and when a compound of formula (I) is desired wherein R is hydrogen, hydrolysing the thus obtained compound of formula (I) wherein R is R'.

Suitable reducing agents are those reducing agents which afford, at least preferably, selective reduction of the chain linking the amino group to the benzene ring without affecting the —COOR' group.

More particularly the reaction between the compounds of formula (II) and (III) is carried out according to different methods and operative conditions which are substantially determined by the nature of the starting compound of formula (II) employed and therefore by the meaning of —W.

Said various methods of preparation are described in detail hereinafter and are designated as Methods (a) to (d).

Method (a)

According to said method, opening of the epoxide of formula (IIa)

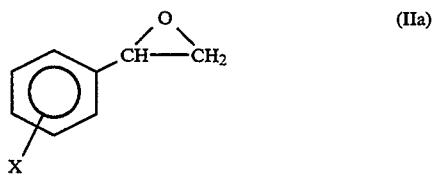   (IIa)

by the amine of formula (III) is carried out in an organic solvent, such as a lower alkanol e.g. methanol, ethanol, and isopropanol, dimethylsulfoxide, a linear or cyclic ether, or an amide, e.g. dimethylformamide or dimethylacetamide, using at least equimolar amounts of the two reactants but preferably an excess of the amine (III). The reaction temperature is comprised between room temperature and the reflux temperature of the selected solvent. A basic condensation agent, such as sodium hydroxide or sodium acetate, may suitably be employed.

Method (b)

In the reaction which comprises condensation of a phenylglyoxal of formula (IIb)

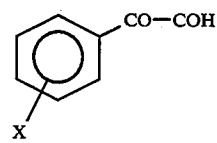   (IIb)

with the amine of formula (III) and reduction of the obtained product, according to a preferred embodiment, said reactions are carried out simultaneously by contacting the compounds (IIb) and (III) in the presence of a suitable reducing agent which is capable of reducing the oxo group to hydroxy without affecting the —COOR' group. As an example said reaction may be suitably carried out by means of sodium borohydride, in an alcoholic solvent, such as ethanol, preferably at low temperatures.

Method (c)

According to still another embodiment, the compounds of formula (I) are obtained by reacting an amine of formula (III) with an α-haloacetophenone of formula (IIc)

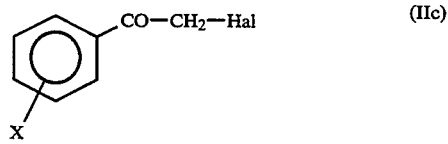   (IIc)

in an inert solvent such as a linear or cyclic: ether, a lower alcohol, e.g. methanol, ethanol or isopropanol, an aromatic hydrocarbon e.g. toluene or benzene, a halogenated aliphatic hydrocarbon e.g. chloroform, or a nitrile e.g. acetonitrile. Said nucleophilic substitution reaction is advantageously carried out at room or lower temperatures.

Reduction of the thus obtained product may then be carried out according to the method described above under item (b).

Method (d)

According to another mode of preparation, the amine (III) is reacted with a compound of formula (IId)

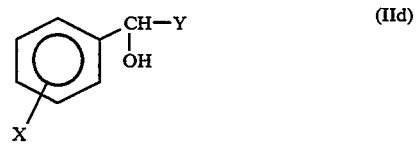   (IId)

wherein X and Y are as defined above.

As functional derivatives of the carboxy group, there may be employed the chloride, the anhydride, mixed anhydrides, active esters, or the suitably activated free acid, e.g. activated with dicyclohexylcarbodiimide (DCCI) or benzotriazolyl-N-oxytris(dimethylamino)-phosphonium hexafluorophosphate (BOP). The reaction between the compound of formula (IId) and the amine (III) is carried out in an aprotic, apolar, or preferably polar organic solvent, such as dimethylformamide, dimethylsulfoxide, methylene chloride, benzene, toluene, optionally in the presence of a proton acceptor agent such as a tertiary aliphatic amine, e.g. triethylamine.

The thus obtained mandelamide of the following formula

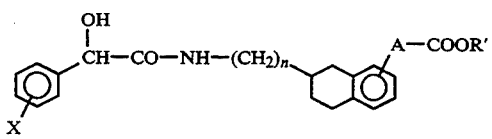

may directly be submitted to reduction of the amido group to methyleneamino.

The reduction step is carried out, as an example, by means of a diborane, i.e. a reactant generating diborane such as the complex between borane and dimethylsulfide, hereinafter designated as "borane-methylsulfide", in an organic solvent such as tetrahydrofuran and at low temperatures (15°–25° C.) to afford preferably reduction of the amido group.

Method (a) will preferably be employed as it does not alter the —COOR' group.

The compounds of formula (I) wherein R is a hydrogen atom may then be easily prepared by saponification of the corresponding esters.

The compounds of formula (I) are isolated according to conventional methods, preferably in the form of the addition salts with mineral or organic acids which allow an easy separation or crystallisation of the obtained compounds, such as picric acid, oxalic acid, or an optically active acid, such as an optionally substituted mandelic acid or a camphorsulfonic acid, or with mineral or organic acids which form pharmaceutically acceptable salts, such as for instance hydrochloric, hydrobromic, sulfuric, phosphoric, methanesulfonic, methylsulfuric, maleic, fumaric, naphthalenesulfonic acids.

The corresponding base may be set free by neutralisation and converted into another acid addition salt thereof or, when R is hydrogen, in a salt with a metal, mainly an alkali or earth-alkaline metal, such as sodium or calcium.

The compounds of formula (I) which only contain the two asymmetric carbons marked by the asterisks may exist as four different isomers. The process of the present invention may afford both pure isomers and race mixtures. More particularly, the reactions described above do not alter the stereochemistry of the compounds involved. Therefore, starting from a compound of formula (IIb) or (IIc) which has no chiral carbon or a compound of formula (IIa) or (IId) as a racemate, and from a compound of formula (III) as a racemate, a mixture of isomers is obtained, i.e. a mixture of the (R,R), (R,S), (S,S), and (S,R) isomers.

Analogously, starting from a pure isomer of a compound of formula (III), such as the R isomer, a mixture of only two isomers is obtained, i.e. the (R,R) and (S,R) isomers. In this case starting, if an optically active isomer of a compound (IIa) or (IId) is also employed, a pure isomer can be obtained.

When a mixture of the four isomers is obtained, it may be separated into two couples of enantiomers (R,R)+(S,S) and (R,S)+(S,R), which are diastereoisomers each other, by suitable techniques such as fractional crystallisation from a suitable solvent, preferably a lower alkanol, such as ethanol, isopropanol and mixtures thereof. Each couple of enantiomers may then be resolved into the pure isomers e.g. by formation of diastereoisomeric salts or by chromatography on chiral columns or any other suitable technique.

When one of the starting compounds is optically active, the mixture of the two diastereoisomers thus obtained is separated into the pure isomers by the techniques cited above.

The starting compounds of formula (II) are known products or anyway they can be prepared by conventional methods described in the chemical literature. As an example, the compounds of formula (IIa) may be prepared by epoxidation of the corresponding styrene derivatives with oxygen in the presence of a silver catalyst, or by reaction of dimethylsulfonium or dimethylsulfoxonium methylylide with the corresponding substituted benzaldehydes according to the method described by E. J. Corey in J.Am. Chem. Soc., 1956, 87,1353.

According to a preferred method of preparation, a compound of formula (IIa) in optically active form may be obtained by reduction of the substituted mandelic acid derivative having the desired absolute configuration at the α-carbon atom into the corresponding glycol derivative, esterification of the primary alcoholic group with a functional derivative of a sulfonic acid, such as tosyl or mesyl chloride, and cyclisation of the thus obtained compound by means of a strong base such as an alkali metal hydroxide under the conditions conventionally employed in intramolecular nucleophilic substitution reactions.

The compounds of formula (IIb) can be easily prepared by the action of an oxidizing agent such as selenium dioxide, on the corresponding acetophenones in water or in an organic solvent such as a cyclic ether e.g. dioxane or tetrahydrofuran.

According to another method of preparation, said compounds of formula (IIb) are obtained by action of dimethylsulfoxide on the haloacetophenones of formula (IIc) having the same substitution on the benzene ring according to the method described by N. Kornblum in J. Am. Chem. Soc., 1957, 79, 6562, or starting from the corresponding α-dihaloacetophenones by the reaction described by F. Venier in C.R.Acad.Sci., 1968, 266, 1656.

The starting compounds of formula (IIc) are easily prepared by halogenation of the corresponding ketones, or, in some cases, by Friedel-Crafts reactions between the corresponding substituted benzene derivatives and a haloacetic acid halide. Finally, mandelic or substituted mandelic acid functional derivatives of formula (IId) are prepared from the corresponding acids which in their turn may be obtained through hydrolysis of the corresponding mandelonitriles. These last compounds may be prepared starting from substituted or unsubstituted benzaldehyde and hydrogen cyanide or from substituted or unsubstituted benzaldehyde, sodium cyanide, and sodium bisulfite according to methods well known in the chemical literature. Mandelic acids of formula (IId) obtained in the form of racemates can be easily separated into their optically active isomers by formation of diastereosiomeric salts with suitably selected optically active bases according to conventional methods and techniques.

The compounds of formula (III), with the exception of those compounds wherein n is 0 and the —A—COOR' group is a —CH₂—COOR' group at position 6 or 7, are new compounds and represent the key intermediates in the preparation of compounds (I). Said compounds of formula (III) represent therefore a further specific object of the present invention.

Preferred compounds of formula (Ill) are those compounds (III) wherein —A—COOR' is linked to the 6- or 7-position of the tetraline ring and A represents a bond between the —COOR' group and the tetraline ring, an alkylene of 2 or 3 carbon atoms, or an alkenylene of 2 carbon atoms.

The compounds of formula (III) may all be prepared starting from an aldehyde of formula (IV)

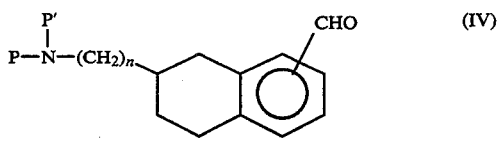

wherein P is a suitably selected temporary protecting group of the amino function and P' is a hydrogen atom or P and P' taken together with the nitrogen atom represent a phthalimido or phthalimido-like protecting group,.

To obtain the compounds of formula (III) wherein A represents a bond between the COOR' group and the tetralin ring, the compound of formula (IV) is oxidised, the free carboxy group is esterified and the protecting group is then cleaved off.

For the preparation of the compounds of formula (III) wherein A is a methylene group the aldehyde of formula (IV) is reacted with 2-(trimethylsilyl)ethoxymethyltriphenylphosphonium chloride, the thus obtained intermediate of formula (V)

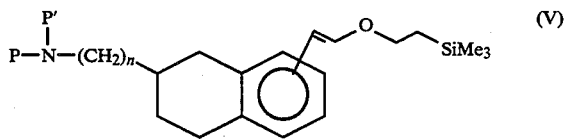

is treated with a tetraalkylammonium fluoride and the same procedure which has been described above is then followed but starting from the thus obtained aldehyde of formula (VI)

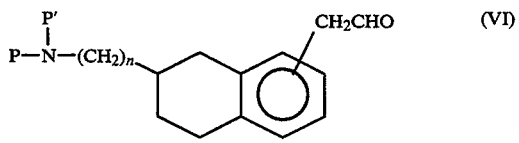

By reaction of the aldehydes (IV) or (VI) with the suitable Wittig compounds which already contain the substituent —COOR', followed by deprotection, the compounds of formula. (III) wherein A is a ($C_2$-$C_4$)alkenylene and R' and n are as defined above are directly obtained and by reduction of the double bond of the thus obtained products the corresponding compounds of formula (III) wherein A represents a ($C_2$-$C_4$)alkylene are obtained.

The compounds of formula (III) wherein A is a branched group can easily be obtained starting from the compounds (III) prepared by the above methods, by the following procedure: protection of the amino group, mono- or di-methylation at the α-position with respect to the —COOR' group, this step being eventually followed by hydrolysis of the ester, Arndt-Eistert reaction which affords the next higher homolog, and esterification of the carboxy group, and then, in both cases, deprotection of the amino group; said compounds may also be obtained starting from the aldehyde (VI) by blocking the —CHO group (e.g. by preparing a Schiff base thereof such as the t-butylimino derivative thereof), mono- or di-methylation of the carbon atom at the α-position with respect to the —CHO group, restoration of the aldehyde function and reaction with the suitable Wittig compound, optionally followed by reduction of the double bond.

Suitable protecting groups will depend on the type of reaction foreseen starting from the aldehyde (IV) and on the selected reaction conditions.

More particularly, when the aldehyde (IV) is submitted to reactions which do not involve strongly acidic conditions, preferred protecting groups are t-alkoxycarbonyl groups, such as t-butoxycarbonyl (BOC) or t-amyloxycarbonyl (AOC), the BOC group being particularly preferred. Cleavage of said protecting groups is then easily achieved by acid hydrolysis according to methods well known in the literature and mainly with trifluoroacetic or hydrochloric acid in alcohols.

Substituted or unsubstituted benzyloxycarbonyl groups may also be employed as protecting groups which are then removed by catalytic hydrogenation preferably using Pd/C as the catalyst.

Finally, when the use of strongly basic substances is foreseen, the amino group may conveniently be protected by formation of a phthalimido derivative which is then splitted off by treatment with hydrazine or substituted hydrazine.

It is always possible, if the selected reaction conditions do require it, to use as the starting compound an aldehyde (IV) wherein the amino group is protected with a given protecting group and then replacing said protecting group with another one which is finally cleaved off as described above.

The person skilled in the art is anyway able to select from the literature (see for instance D. Barton and W. D. Ollis, Comprehensive Organic Chemistry, Vol. 5, pp. 323-331 and the references cited therein) protecting groups which can suitably be employed under the reaction conditions foreseen.

Oxidation of the aldehyde (IV) to convert the —CHO group into carboxy, may conveniently be carried out at room temperature, using as the oxidizing agent the Jones reagent which consists of a solution of chromic anhydride in diluted sulfuric acid. The reaction is generally carried out by adding the Jones reagent to a solution of the starting aldehyde in acetone. The thus obtained acid is isolated by conventional procedures and esterified by treatment with a ($C_1$-$C_4$)alkyl chloroformate in the presence of a tertiary amine that is used as acceptor of the acid which forms during the reaction. The reaction is preferably carried out at a temperature of from $-10°$ C. to $+10°$ C., in an aprotic organic solvent such as a halogenated hydrocarbon. Deprotection of the amino group is then carried out by classical methods. When, according to a preferred embodiment, a BOC group is employed, this group is easily removed by treatment of an alcoholic solution of the protected product with 4N alcoholic HCl.

Conversion of the aldehyde (IV) into the aldehyde (VI) is advantageously carried out by treating the aldehyde (IV) with a solution of 2-(trimethylsilyl)ethoxymethyltriphenylphosphonium chloride and an alkali metal alcoholate in an aprotic organic solvent namely an alkyl or cyclic ether such as tetrahydrofuran or dimethoxyethane, isolating the intermediate product of formula (V) by conventional methods and treating said intermediate with a tetraalkylammonium fluoride in a polar, aprotic organic solvent which may suitably contain a small amount of water.

The aldehydes of formulas (IV) and (VI) may then be submitted to the Wittig reaction as modified by W. S. Wadsworth and W .D. Emmons (J.Amer.Chem.Soc., 1961, 83, 1733–38) which involves reaction with a carboxymethylphosphonate of formula $(EtO)_2P(O)CH(R'')$—COOR', wherein R' is as defined above and R" is a hydrogen atom, a methyl group or an ethyl group, in the presence of a strong base, such as an alkali metal hydride, in an aprotic organic solvent, typically dimethoxyethane or tetrahydrofuran.

When the —COOR' group is not linked directly to the carbon atom of the phosphonate, the corresponding Wittig reactant of formula $Ph_3P=CH-A'-COOR'$ is preferably employed wherein A' is an alkylene of 1 or 2 carbon atoms and R' is as defined above, generally in the presence of a strong base, such as NaH or $(nC_4H_9)Li$, in an aprotic solvent such as an alkyl or cyclic ether.

By these processes there may be obtained the compounds of formula (III) wherein A is a $(C_2-C_4)$alkenylene group and R' is as defined above are thus obtained. If desired, these compounds may then he converted into the corresponding compounds wherein A is a $(C_2-C_4)$alkylene by reduction of the double bond. Said reduction may suitably be carried out by catalytic hydrogenation at room temperature and ordinary pressure using Pd/C as the hydrogenation catalyst. When a benzyloxycarbonyl or a substituted benzyloxycarbonyl group is employed to protect the amino group, in one and the same step removal of said protecting group is also achieved.

If necessary, mono- or di-methylation of the carbon atom at the α-position with respect to the carbalkoxy group, may be achieved by treating the compounds of formula (III), obtained as described above, following protection of the amino group, with a methyl halide, typically methyl iodide, in the presence of a strong base. The thus obtained compounds may then be converted into the next higher homologs by hydrolysis of the —COOR' group in basic conditions, Arndt-Eistert reaction (Ber., 1935, 68, 200) which involves conversion of the acid into the corresponding acid chloride, followed by reaction of this last product with diazomethane and hydrolysis of the obtained compound in the presence of $Ag_2O$, esterification of the carboxy group and finally deprotection of the amino group.

When starting from the aldehyde (VI), before carrying out the methylation reaction, it is necessary to block the —CHO by converting it into a Schiff base, for instance into the t-butylimino derivative thereof, by reaction with a primary amine, for instance t-butylamine. Methylation is then carried out as described above, the aldehyde is restored by mild acid hydrolysis, and the —CHO group is oxidised to carboxy which is then esterified; or, alternatively, said aldehyde is reacted with a Wadsworth and Emmons compound and the double bond is optionally reduced as described above.

If desired the racemic mixtures of the compounds of formula (III) thus obtained are resolved into the pure isomers by formation of the diastereoisomeric salts with optically active adds such as camphorsulfonic acids, optionally substituted mandelic acids and the like optically active acids.

Alternatively, it is also possible to hydrolyse the ester and resolve the racemic mixture into optically pure isomers by formation of diastereoisomeric salts with optically active organic bases, such as α-alkylbenzylamines, menthylamine, or the like bases conventionally employed in the art.

If the amine (III) contains an additional chiral centre the diastereoisomers and the four pure isomers may be isolated as described above and employed for the preparation of the isomers of the compounds (I).

In its turn the aldehyde (IV) is prepared starting from the corresponding 2-amino- or 2-aminomethyl-5 or 6 or 7 or 8-hydroxytetraline by a four step process which involves firstly protection of the amino group, reaction of the protected amine with trifluoromethanesulfonic anhydride, conversion of the thus obtained corresponding N-protected 2-amino- or 2-aminomethyl-5 or 6 or 7 or 8-trifluoromethanesulfonyloxy-tetraline into the corresponding N-protected 2-amino- or 2-aminomethyl-5 or 6 or 7 or 8-vinyltetraline with $[CH_3(CH_2)_3]_3SnCH=CH_2$ in the presence of tetrakis(triphenylphosphine)palladium and oxidation of the vinyl derivative with an alkali metal periodate catalysed by $OsO_4$.

Starting from one of the isomers of 2-amino- or 2-aminomethyl-5 or 6 or 7 or 8-hydroxytetralin, compounds generally known in the literature and that in any case can be prepared by known methods, the isomer of the aldehyde (IV) with the same absolute configuration is obtained.

The pure isomers of the aldehyde of formula (IV) are preferred and represent a further object of the present invention.

The compounds of formula (I) and their salts showed very interesting pharmacological properties as antidepressant agents.

More particularly the antidepressant properties of the compounds of formula (I) have been studied in the test of the antagonism of apomorphine-induced hypothermia, a test conventionally employed in psychopharmacology and generally considered predictive of antidepressant activity in humans.

Possible behavioural and locomotor activity modifications in mice following administration of increasing doses of test compounds have also been evaluated.

The effects shown by the compounds of formula (I) which are able to antagonise the hypothermia induced in mice by high doses of apomorphine, are clearly indicative of an antidepressant activity in humans.

The compounds of formula (I) furthermore do not elicit any sedation or any decrease of spontaneous locomotor activity in mice.

The test has been carded out as follows:
Antagonism of apomorphine-induced hypothermia (A. J. Puech et al., Psychopharmacology, 75(1), 84–91,1981)

Male CD1 mice (Charles River-France) weighing 22–25 g were used in the test. The mice were housed individually in transparent plastic cages. The test compounds were suspended in 1% aqueous carboxymethylcellulose. They were administered intraperitoneally (10 ml/kg; 6 mice per dose). Control animals received the vehicle only. Rectal temperature was measured using a probe carrying a thermoelectric couple (connected to a galvanometer) inserted to a constant depth.

The compounds to be tested as well as the vehicle were administered 30 minutes after basal rectal temperature was measured and 30 minutes later apomorphine (16 mk/kg) was administered subcutaneously. Rectal temperature was measured again 30 minutes after the administration of apomorphine.

The compounds of formula (I) antagonise the effects of apomorphine at doses as low as 0.03–1 mg/kg i.p.

Motor activity

At the same doses the compounds of formula (I) almost do not affect motor activity, the compounds of Examples 2 and 5 being completely ineffective also at 10 mg/kg i.p.

The compounds of formula (I) proved also to be active as intestinal motility modulating agents.

Their effects in reducing colon spontaneous motility have been observed in vitro normalized pharmacological tests.

In the in vitro tests the capability of different concentrations of the compounds of formula (I) to reduce, under particular normalised conditions, the spontaneous contractile activity of isolated proximal colon rat strips has been evaluated.

Not fasted male rats weighing 250–300 g are sacrificed. The proximal part of the colon, approximately a 2 to 3 cm segment, is removed and suspended in a 20-ml organ bath containing oxygenated (5% $CO_2$, 95% $O_2$) Krebs-Ringer solution with the following mM composition: NaCl 118.4; KCl 4.7; $CaCl_2$ 2.45; $MgSO_4$ 1.16; $NaH_2PO_4$ 3.7: glucose 5.6: $NaHCO_3$ 30.9; kept at a constant temperature of 37° C. The colon strips submitted to a 1 g traction spontaneously contract. The test compounds are added thereto after stabilisation of the preparation (2 h).

The $EC_{50}$, i.e. the concentration which is effective to reduce by 50% the contractile activity observed in controls, is determined.

In this test the compounds of the present invention showed a very high activity characterised, for the most active compounds, by $EC_{50}$s in the range of 0.5 to 50 nM.

The compounds of formula (I) showed also a surprising specificity towards the colon. In vitro tests, carried out by the same general method but on isolated rat uterus, showed that a significative effect on spontaneous uterus motility is obtained at doses much higher than those active on colon.

The compounds of formula (I) and their pharmaceutically acceptable salts have also a very low toxicity, compatible with the utilisation of these products as drugs.

Thus, in another of its embodiments, the present invention concerns the pharmaceutical compositions comprising, as the active principle, one or more compounds of formula (I) or their pharmaceutically acceptable salts.

The pharmaceutical compositions of the present invention may be prepared for oral, sublingual, subcutaneous, intramuscular, intravenous, transdermal or rectal administration of the active principles of formula (I), preferably in unit dosage forms, in admixture with conventional pharmaceutical vehicles.

Said unit dosage forms generally contain from 0.1 to 500 mg, and preferably from 0.5 to 250 mg of active principle per unit dosage form.

Suitable unit dosage forms for the oral administration comprise tablets, capsules, powders, and oral solutions and suspensions.

When a solid composition is prepared in tablet form, the main active ingredient is mixed with a pharmaceutical vehicle such as gelatine, starch, lactose, magnesium stearate, talc, arabic gum, and the like. Tablets may be coated with sucrose or other suitable materials or they may be treated so that their activity is extended or delayed and that they continuously release a predetermined amount of active principle.

A preparation in capsules is obtained by mixing the active ingredient with a diluent and a lubricant and by filling soft or hard capsules with the thus obtained mixture.

A Liquid preparation in the form of syrup or elixir or for the administration in drops may contain the active ingredient jointly with a possibly acaloric sweetener, methylparaben, and propylparaben as antiseptics, as well as a flavoring agent and a suitable dye.

Water-dispersible powders or granules may contain the active ingredient mixed with dispersing, wetting, or suspending agents, such as polyvinylpyrrolidone, and with sweetening or flavoring agents.

For rectal administration suppositories are prepared with binding agents melting at metal temperature for example cocoa butter or polyethyleneglycols.

For parenteral administration, aqueous suspensions, isotonic saline solutions, or sterile injectable solutions are employed which contain pharmacologically compatible dispersing and/or wetting agents, for example propyleneglycol or butyleneglycol.

The active principle may also be formulated in the form of microcapsules or microemulsions, possibly with one or more supports or additives.

The main active principle of formula (I) may be administered in the form of free base or as a pharmaceutically acceptable salt thereof, as such or as a complex with, for instance, a cyclodextrine, or even in association or co-administration with other active principles.

The following examples further illustrate the invention without however limiting it. The solvents indicated between parentheses after the melting point represent the crystallisation solvents.

PREPARATION I 2-amino-7-(2-ethoxycarbonyl)vinyl-tetraline hydrochloride a) 2-tertbutoxycarbonylamino-7-trifluoromethanesulfonyloxy-tetraline A mixture of 2-tertbutoxycarbonylamino-7-hydroxytetraline (24 g, 0.09 mol) and pyridine (50 ml) is cooled to 0° C. under nitrogen atmosphere and trifluoromethanesulfonic anhydride (16.4 ml, 0.10 mol) is added thereto. After 10 minutes at 0° C., the reaction temperature is allowed to rise to room temperature. Alter 2.5 hours the reaction mixture is poured into water and extracted with ethyl ether.

The organic phase is washed with 1N HCl and then with water, dried over sodium sulfate and concentrated under vacuum.

The dark oily product which is obtained is purified by silica gel column chromatography eluting with petroleum ether:ethyl acetate 9:1 affording 25 g of the compound indicated above. M.p. 87°–89° C.

b.) 2-tertbutoxycarbonylamino-7-vinyl-tetraline

A mixture of the compound obtained in step a) above (25 g, 0.063 tool), anhydrous dioxane (280 ml), tributyl-vinyl-tin (19.3 ml, 0.066 mol), LiCl (8.141 g), $Pd(Ph_3P)_4$ (1.483 g) and few crystals of 2,6-di-tertbutyl-4-methylphenol, under nitrogen atmosphere is refluxed for 3 hours and then cooled to room temperature. Pyridine (32 ml) and 1M tetrabutylammonium fluoride in tetrahydrofuran (90 ml) are then added thereto. After 16 hours at room temperature, ethyl ether is added and the mixture is filtered on celite. The organic solution is washed with water, 1N HCl, and water, then it is dried over sodium sulfate and concentrated to dryness. The thus obtained oily product is purified by silica gel column chromatography eluting with cyclohexane:ethyl acetate 9:1, affording 10 g of 2-tertbutoxycarbonylamino-7-vinyl-tetraline. M.p. 104°–105° C. (isopropyl ether).

c) 7-formyl-2-tertbutoxycarbonylamino-tetraline

A mixture of the compound obtained in step b) above (2.5 g, 0.009 mol), sodium periodate (6 g), 2.5% osmium tetroxide in tertbutanol (3.3 ml), tetrahydrofuran (60 ml), and water (20 ml) is stirred at room temperature under nitrogen atmosphere for 3 hours. The reaction mixture is then poured into water and extracted with ethyl acetate. The organic solution is washed with water, dried over sodium sulfate and concentrated under vacuum. The dark oily product which is thus obtained is purified by silica gel column chromatography eluting with a mixture petroleum ether:ethyl acetate 95:5.

An oily residue is obtained which solidifies on standing and which is crystallised from isopropyl ether. Yield: 1.7 g.

d) 2-tertbutoxycarbonylamino-7-(2-ethoxycarbonyl)-vinyl-tetraline

A mixture of 80% sodium hydride (0.6 g, 0.024 mol), ethyl diethylphosphonacetate (4.8 ml), and dimethoxyethane (50 ml) is stirred at room temperature and under nitrogen atmosphere for 1 hour, then a solution of the compound obtained in step c) above (3.4 g) in dimethoxyethane (65 ml) is slowly dripped in. After 4 hours at room temperature, water is added and the mixture is extracted with ethyl ether. The organic phase is washed with water, dried over sodium sulfate and concentrated under vacuum. A yellow oil (3.1 g) is obtained which is purified by silica gel column chromatography eluting first with a mixture cyclohexane:ethyl acetate 9:1 and then with a mixture of the same solvents in a 8:2 ratio. Yield: 2.7 g. M.p. 110°–111° C. (isopropyl ether).

e) 2-amino-7-(2-ethoxycarbonyl)vinyl-tetraline hydrochloride

A solution of the compound obtained in step d) above (2.7 g, 0.0078 mol) in absolute ethanol (50 ml) is allowed to react at room temperature for 5 hours with 4N HCl absolute ethanol (33 ml).

The mixture is then concentrated under vacuum and the residue is dried in the oven affording the compound indicated in the title (2.05 g). M.p. 184°–186° C.

PREPARATION II 2-amino-7-(2-ethoxycarbonyl)ethyl-tetraline hydrochloride a) 2-tertbutoxycarbonylamino-7-(2-ethoxycarbonyl)ethyl-tetraline A mixture of the compound obtained in Preparation I step d) (2.6 g, 0.075 mol), absolute ethanol (60 ml) and 5% Pd/C (0.26 g) is charged into a hydrogenation flask. Hydrogenation is carried out at room temperature and ordinary pressure for 2.5 hours, then the reaction mixture is filtered on celite and the filtrate is concentrated under vacuum affording 2.2 g of 2-tertbutoxycarbonylamino-7-(2-ethoxycarbonyl)ethyltetraline. M.p. 110°–11 ° C.

b) 2-amino-7-(2-ethoxycarbonyl)ethyl-tetraline hydrochloride

A mixture of the compound obtained in step a) above (2.1 g, 0.006 tool), absolute ethanol (40 ml) and 4N HCl in absolute ethanol (25 ml) is reacted at room temperature for 5 hours. The white solid obtained by concentrating the reaction mixture under vacuum is dried in the oven affording 1.7 g of the compound of the title. M.p. 162°–164° C.

PREPARATION III 2-amino-7-ethoxycarbonyl-tetraline hydrochloride a) 7-ethoxycarbonyl-2-tertbutoxycarbonylamino-tetraline Jones reagent (a solution of chromic anhydride in diluted sulfuric acid) (8 ml) is added to a mixture of the compound obtained in Preparation I step c) (1.55 g) and acetone (15 ml) kept at 20° C. After 5.5 hours, isopropanol is added thereto and the mixture is filtered. The filtrate is concentrated under vacuum, the residue is taken up in water and NaOH is added to the aqueous solution to make it basic. The solution is extracted with ethyl ether, then it is acidified with HCl and extracted again twice with ethyl ether. The organic extracts are combined, washed with water, dried over sodium sulfate and concentrated under vacuum yielding 1.5 g of a solid yellow product.

A mixture of the thus obtained product, methylene chloride (20 ml) and triethylamine (0.79 ml) is cooled to 0° C. and ethyl chloroformate (0.55 ml, 0.0057 mol) and, 5 minutes later, dimethylaminopyridine (0.32 g) are then added thereto. After 30 minutes at 0° C., the reaction mixture is poured into water and methylene chloride is added thereto. The organic phase is separated, and washed sequentially with aqueous sodium bicarbonate, 1N HCl, and water. The organic solution is then dried over sodium sulfate and concentrated under vacuum affording an oily residue which is purified by silica gel column chromatography eluting first a mixture cyclohexane:ethyl acetate 9:1 and then with a mixture of the same solvents in a 8:2 ratio. Yield :0.52 g.

$^1$H NMR (80 MHz, CDCl$_3$) $\delta$7.6(m,2H), 7(m, 1H), 4.25(q,2H), 4.4(1H,—NH—), 3.8(m, 1H), 1.3(m,12H).

b) 2-amino-7-ethoxycarbonyl-tetraline hydrochloride

A mixture of the compound obtained in step a) above (0.5 g, 0.0016 mol), absolute ethanol (10 ml) and 4N HCl ethanol (7 ml) is reacted at room temperature for 24 hours. Upon concentrating under vacuum, a pale yellow oil is obtained which solidifies by treatment with isopropanol. The solid is recovered by filtration affording 0.29 g of the compound of the title.

$^1$H NMR (80 MHz, DMSO-d$_6$) $\delta$8.4(—NH$_2$ HCl), 7.6(m,2H), 7.1(m, 1H), 4.2(q,2H), 1.3(t,3H).

PREPARATION IV (2R) 2-amino-7-(2-ethoxycarbonyl)vinyl-tetraline hydrochloride a) (2R) 7-hydroxy-2-tertbutoxycarbonylamino-tetraline A suspension of (2R) 2-amino-7-hydroxy-tetraline (9.4 g, 0.058 mol) in triethylamine (39.5 ml. 0.28 mol) and anhydrous dimethylformamide ( 100 ml) is cooled to 0° C. Di-tertbutyl-dicarbonate (13.6 g, 0.063 mol) is added thereto and the reaction mixture is allowed to stand at room temperature for 2 hours. It is then poured into water (500 ml), and extracted with ethyl ether which is washed with water, dried and evaporated to dryness. The thus obtained product is purified by flash chromatography eluting with a mixture cyclohexane:ethyl acetate 7:3, affording 12.7 g of the compound indicated above $[\alpha]_D^{20} = +69.3°$ (c=1%,MeOH).

b) (2R)2-tertbutoxycarbonylamino-7-trifluoromethanesulfonyloxy-tetraline

A mixture of the compound obtained in step a) above (12.4 g, 0.047 mol) and pyridine (2.5 ml) is cooled to 0°

C. under nitrogen atmosphere and trifluoromethanesulfonic anhydride (8.5 ml, 0.052 mol) is added thereto in 25 minutes while keeping the temperature between 0° and 5° C. The reaction mixture is stirred at room temperature for 2.5 hours and then poured into water (400 ml). The mixture is extracted with ethyl ether, the organic phase is dried, filtered and evaporated to dryness. The thus obtained residue is purified by flash chromatography eluting with a mixture cyclohexane:ethyl acetate 85:15 and cooling the oily product which is obtained by evaporating off the collected fractions. Yield: 15 M.p. 52°–55° C. $[\alpha]_D^{20} = +48.3°$ (c=1%. MeOH).

c) (2R) 2-tertbutoxycarbonylamino-7-vinyl-tetraline

The compound is obtained by following the procedure described in Preparation I step b) but starting from the product obtained in step b) above. Yield: 7 g. M.p. 89°–91° C. (isopropyl ether). $[\alpha]_D^{20} = +40°$ (c=0.3%, $CH_2Cl_2$).

d) (2R) 7-formyl-2-tertbutoxycarbonylamino-tetraline

The compound is obtained by following the procedure described in Preparation I, step c) but starting from the compound obtained in foregoing step c) and purifying the thus obtained product by flash chromatography eluting with a mixture hexane:ethyl acetate 7:3. Yield: 4.9 g. M.p. 98°–100° C. $[\alpha]_D^{20} = +41.5°$ (c=0.3%, $CH_2Cl_2$).

e) (2R) 7-(2-ethoxycarbonyl)vinyl-2-tertbutoxycarbonylamino-tetraline

This compound (3.3 g) is obtained by following the procedure described in Preparation I step d) but starting from the compound of step d) above. M.p. 107°–108° C. (cyclohexane). $[\alpha]_D^{20} = +35.2°$ (c=0.3%, $CH_2Cl_2$).

f) (2R) 2-amino-7-(2-ethoxycarbonyl)vinyl-tetraline hydrochloride

The compound of the title is obtained by following the procedure of Preparation I step e), but starting from the compound obtained in step e) above. M.p. 204°–206° C. $[\alpha]_D^{20} = +52.3°$ (c=1%, MeOH).

PREPARATION V (2R) 2-amino-7-( 2-ethoxycarbonyl )ethyl-tetraline hydrochloride a) (2R) 7-(2-ethoxycarbonyl)ethyl-2-tertbutoxycarbonylamino-tetraline The above compound (0.7 g) is obtained by following the procedure described in Preparation II step a) but starting from the compound prepared in Preparation IV step e) (0.75 g, 0.0021 mol). M.p. 101°–102° C. $[\alpha]_D^{20} = +0.3°$ (c=0.3%, $CH_2Cl_2$).

b) (2R) 2-amino-7-(2-ethoxycarbonyl)ethyl-tetraline hydrochloride

The compound indicated in the title (0.4 g) is obtained by following essentially the procedure described in Preparation II step b ), but starting from the compound obtained in step a)above (0.6 g, 0.0017 mol). M.p. 175°–78° C. (acetone). $[\alpha]_D^{20} = +45.6°$ (c=0.3%, $CH_2Cl_2$).

PREPARATION VI (2S) 2-amino-7-(2-ethoxycarbonyl )vinyl-tetraline hydrochloride

The compound indicated in the title (m.p. 200°–203° C. from acetone) is prepared by following the procedure described in Preparation IV but starting from (2S) 2-amino-7-hydroxytetraline and via the following intermediates:

a) (2S) 7-hydroxy-2-tertbutoxycarbonylamino-tetraline $[\alpha]_D^{20} = -62.4°$ (c=1%, MeOH).

b) (2S)2-tertbutoxycarbonylamino-7-trifluoromethanesulfonyloxy-tetraline $[\alpha]_D^{20} = -43.1°$ (c=1%, MeOH).

c) (2S)2-tertbutoxycarbonylamino-7-vinyl-tetraline M.p. 90°–92° C. (isopropyl ether). $[\alpha]_D^{20} = -38.1°$ (c=0.3%, $CH_2Cl_2$).

d) (2S) 7-formyl-2-tertbutoxycarbonylamino-tetraline M.p. 98°–101° C. $[\alpha]_D^{20} = -45.5°$ (c=0.3%, $CH_2Cl_2$).

e) (2S) 7-(2-ethoxycarbonyl)vinyl-2-tertbutoxycarbonylamino-tetraline M.p. 106°–108° C. (isopropyl ether). $[\alpha]_D^{20} = +36.1°$ (c=0.3%, $CH_2Cl_2$).

PREPARATION VII (2S) 2-amino-7-(2-ethoxycarbonyl )ethyl-tetraline hydrochloride a) (2S) 7-(2-ethoxycarbonyl)ethyl-2-tertbutoxycarbonylamino-tetraline The above compound is obtained by following the procedure described in Preparation II step a) but starting from the compound prepared in Preparation IV. M.p. 100°–102° C. (isopropyl ether). $[\alpha]_D^{20} = +3.7°$ (c=0.3%, $CH_2Cl_2$).

b) (2S) 2-amino-7-(2-ethoxycarbonyl )ethyl-tetraline hydrochloride

The compound indicated in the title is obtained by following essentially the procedure described in Preparation II step b ), but starting from the compound obtained in step a)above. Yield: 60%.M.p. 178°–80° C. $[\alpha]_D^{20} = -44.8°$ (c=0.3%, $CH_2Cl_2$).

PREPARATION VIII 2-amino-7-(3-ethoxycarbonyl)allyl-tetraline hydrochloride a) 7-formylmethyl-2-tertbutoxycarbonylamino-tetraline A mixture of potassium tertbutylate (1.1 g, 9.9 mmol) and anhydrous tetrahydrofuran (130 ml) is cooled to −60° C. under nitrogen atmosphere and 2-(trimethylsilyl)ethoxymethyltriphenylph chloride (4.7 g, 10.8 mmol) is then added thereto. After 10 minutes at −60° C., the temperature is allowed to rise while stirring for 10 minutes. A solution of the compound obtained in Preparation I step c) (1 g, 3.6 mmol) in tetrahydrofuran (10 ml) is then slowly dripped in. The reaction mixture is stirred for 20 minutes then it is poured into ice/water (200 ml) and extracted with ethyl ether. The organic extract is dried over sodium sulfate, filtered and concentrated under vacuum. The thus obtained residue is purified by flash chromatography eluting with a mixture cyclohexane:ethyl acetate 9:1. A yellow oily product (1.2 g) is obtained that corresponds to 2-tertbutoxycarbonylamino-7-[2-(2-(trimethylsilyl)ethoxy)vinyl]tetraline.

A 1.1M solution of tetrabutylammonium fluoride (20 ml) is added to a solution of the thus obtained product (2.56 mmol) in acetonitrile (19.5 ml) and water (0.5 ml) and the reaction mixture is heated to 80° C. for 30 minutes under nitrogen atmosphere, then cooled and poured into water (150 ml). The mixture is extracted with ethyl ether, the extracts are dried over sodium sulfate, filtered and concentrated to dryness. The residue is purified by flash chromatography eluting with a mixture cyclohexane:ethyl acetate 8:2 affording 100 mg of the compound indicated above.

b) 7-(3-ethoxycarbonyl)allyl-2-tertbutoxycarbonylamino-tetraline

This product is obtained by following the procedure described in Preparation I step d) but starting from the compound obtained in step a) above.

c) 2-amino-7-(3-ethoxycarbonyl)allyl-tetraline hydrochloride

The compound of the title is obtained by following the procedure described in Preparation I step e) but starting from the compound obtained in step b) above.

PREPARATION IX 2-amino- 7-(3-ethoxycarbonyl)propyl-tetraline hydrochloride a) 7-(3-ethoxycarbonyl)propyl-2-tertbutoxycarbonylamino-tetraline This product is obtained by following the procedure described in Preparation II step a) but starting from the compound obtained in Preparation VIII step b).

b) 2-amino-7-(3-ethoxycarbonyl)propyl-tetraline hydrochloride

The compound of the title is obtained by following the procedure described in Preparation II step b) but starting from the compound obtained in step a) above.

PREPARATION X (2R)2-amino-7-ethoxycarbonyl-tetraline hydrochloride a) (2R) 7-ethoxycarbonyl-2-tertbutoxycarbonylamino-tetraline A solution of 80% $NaClO_2$(920 mg, 8.13 mmol) and $NaHPO_4.5H_2O$ (730 mg, 5.3 mmol) in water (5 ml) is added to a solution of (2R) 7-formyl-2-tertbutoxycarbonylamino-tetraline (200 mg, 0.73 mmol) obtained in Preparation IV, step d) in tert-butanol (7 ml).

The reaction mixture is stirred vigorously at room temperature for 1 hour, brought to pH~3 by the addition of 1N HCl and extracted with ethyl acetate. The organic phase is dried over sodium sulfate, filtered and evaporated to dryness. The thus obtained residue is dissolved in a mixture of methylene chloride (10 ml) and triethylamine (0.11 ml), the solution is cooled to 0° C. and ethyl chloroformate (80 µl) and, 5 minutes later, 4-dimethylaminopyridine (50 ng) are slowly dripped in. After 1 hour at 0° C. the reaction mixture is poured into water and extracted with ethyl acetate. The organic phase is washed sequentially with 1N HCl water, saturated sodium bicarbonate, and water, dried over sodium sulfate, filtered and concentrated to dryness. The thus obtained residue is purified by flash chromatography eluting with a mixture cyclohexane:ethyl acetate 75:25 affording 200 mg of the above indicated product. M.p. 125°–28° C.

b) (2R) 2-amino-7-ethoxycarbonyl-tetraline hydrochloride 8.4N HCl ethanol (7 ml) is added to a solution of the compound obtained in step a) above (600 mg, 1.9 mmol) in ethanol (20 ml) and the reaction mixture is allowed to stand at room temperature for 5 hours and then evaporated to dryness. The thus obtained residue is taken up by triturating it with hot acetone (10 ml), cooled and filtered affording 350 mg of the compound indicated in the title. M.p. 185°–88° C. $[\alpha]_D^{20} = -54.8°$ (c=0.3%, MeOH).

PREPARATION XI (2S) 2-amino- 7-ethoxycarbonyl-tetraline hydrochloride

The compound of the title (m.p. 189°–91 ° C.; $[\alpha]_D^{20} = -52.420°$ (c=0.3%, MeOH)) is obtained by following the procedure described in Preparation X but starting from (2S) 7-formyl-2-tertbutoxycarbonylamino-tetraline obtained in Preparation VI step d) and via the following intermediate:

a) (2S) 7-ethoxycarbonyl-2-tertbutoxycarbonylamino-tetraline. M.p. 124°–125° C.

PREPARATION XII 2-aminomethyl-7-(2-ethoxycarbonyl )vinyl-tetraline hydrochloride a) 2-tertbutoxycarbonylaminomethyl-7-trifluoromethanesulfonyloxy-tetraline A mixture of 2-tertbutoxycarbonylaminomethyl-7-hydroxytetraline (15.9 g, 0.071 mol) described in step (i) of Preparation K of EP-A-436,435 and pyridine (45 ml) is cooled to 0°–5° C. under nitrogen atmosphere and trifluoromethanesulfonic anhydride (13 ml, 0.08 mol) is added thereto in 30 minutes. The reaction temperature is allowed to rise to room temperature. After 4 hours the reaction mixture is poured into a mixture of ice/diluted HCl and the slightly acidic mixture is extracted with ethyl acetate.

The organic phase is washed with water, dried over sodium sulfate and concentrated to dryness.

The product which is thus obtained is purified by flash chromatography eluting with a mixture petroleum ether:ethyl acetate 9:1. The oily product which is obtained solidifies after one night at 4° C. and is crystallised from petroleum ether (80 ml) affording 16.7 g of the compound indicated above. M.p. 65°–67° C.

b) 2-tertbutoxycarbonylaminomethyl-7-vinyl-tetraline

A mixture of the compound obtained in step a) above (500 mg, 1.22 mmol), anhydrous dioxane (5 ml), tributyl-vinyl-tin (0.5 ml, 1.7 mmol), LiCl (150 mg), $Pd(Ph_3P)_4$ (30 mg) and few crystals of 2,6-di-tertbutyl-4-methyl-phenol, under nitrogen atmosphere is refluxed for 3 hours and then cooled to room temperature. Ethyl ether is added and the mixture is filtered on celite. The organic solution is washed with water, dried over sodium sulfate and concentrated under vacuum. The thus obtained oily product is purified by flash chromatography eluting with cyclohexane:ethyl acetate 95:5 and crystallised from petroleum ether, thus affording 0.2 g of 2-tertbutoxycarbonylaminomethyl-7-vinyl-tetraline. M.p. 98°–100° C.

c) 7-formyl-2-tertbutoxycarbonylaminomethyl-tetraline

A 2.5% solution of osmium tetroxide in tertbutanol (2 ml) is added to a mixture of the compound obtained in step b) above (1.4 g, 0.0049 mol), sodium periodate (3.5 g), tetrahydrofuran (40 ml), and water (10 ml). The reaction mixture is stirred at room temperature under nitrogen atmosphere for 1 hour, poured into water and extracted with ethyl acetate. The organic solution is washed with water, dried over sodium sulfate and concentrated under vacuum. The dark oily product which is thus obtained is purified by chromatography eluting with a mixture cyclohexane:ethyl acetate 6:4.

An oily residue is obtained which solidifies by treatment with petroleum ether. Yield: 0.65 g. M.p. 92°–94° C.

d) 2-tertbutoxycarbonylaminomethyl-7-(2-ethoxycarbonyl)vinyl-tetraline

Triethylphosphonacetate (3.5 ml) is added in 20 minutes to a suspension of 60% sodium hydride (0.7 g, 0.175 mol) in dimethoxyethane (30 ml) under nitrogen atmosphere. After stirring at room temperature for 1 hour, a solution of the compound obtained in step c) above (2.5 g) in dimethoxyethane (20 ml) is stirred in, in 10 minutes. After 1 hour at room temperature, water (400 ml) is added and the mixture is extracted with ethyl acetate. The organic phase is washed with water, dried over sodium sulfate and concentrated under vacuum. The obtained product is purified by flash chromatography eluting with a mixture cyclohexane:ethyl acetate 8:2. Yield: 2.8 g. M.p. 117°–119° C. (ethyl ether:ethyl acetate 7:1).

e) 2-aminomethyl-7-(2-ethoxycarbonyl)vinyl-tetraline hydrochloride

A solution of the compound obtained in step d) above (0.7 g, 0.002 mol) in absolute ethanol (40 ml) is allowed to react at room temperature for 4 hours with a solution of hydrogen chloride saturated ethanol (10 ml).

The mixture is then concentrated under vacuum and the residue is crystallised from isopropanol affording the compound indicated in the title (0.35 g). M.p. 215°–218° C.

PREPARATION XIII 2-aminomethyl-7-(2-ethoxycarbonyl)ethyl-tetraline hydrochloride a) 2-tertbutoxycarbonylaminomethyl-7-(2-ethoxycarbonyl)ethyl-tetraline A mixture of the compound obtained in Preparation XII step d) (1.45 g, 0.0{)4 mol), absolute ethanol (50 ml) and 5% Pd/C (0.15 g) is charged into a hydrogenation flask. Hydrogenation is carried out at room temperature and ordinary pressure for 3 hours, then the reaction mixture is filtered on celite, the filtrate is concentrated under vacuum and petroleum ether is added to the oily residue, thus affording, upon filtration, 1.2 g of 2-tertbutoxycarbonylaminomethyl-7-(2-ethoxycarbonyl)ethyl-tetraline. M.p. 69°–71° C. (petroleum ether:isopropyl ether 5:3).

b) 2-aminomethyl-7-(2-ethoxycarbonyl)ethyl-tetraline hydrochloride

A mixture of the compound obtained in step a) above (0.9 g, 0.0025 mol), absolute ethanol (45 ml) and hydrogen chloride saturated ethanol (15 ml) is reacted at room temperature for 4 hours. The mixture is then concentrated under vacuum and the residue is crystallised from isopropanol. Yield: 0.54 g. M.p. 174°–175° C.

PREPARATION XIV 2-aminomethyl-7-ethoxycarbonyl-tetraline hydrochloride

A solution of 80 % sodium chlorite (1.8 g, 16 mmol) and NaH$_2$PO$_4$ (1.6 g, 11.6 mmol) in water (8 ml) is added to a solution of the compound obtained in Preparation XII step c) (500 mg, 1.73 mmol) in tertbutanol (25 ml). The reaction mixture is stirred at room temperature for 1.5 hours and diluted HCl is added thereto up to pH$\sim$3. The solution is extracted with ethyl acetate which is then dried over sodium sulfate, filtered and concentrated to dryness. The thus obtained residue is dissolved in absolute ethanol (20 ml) and hydrogen chloride is then bubbled therein at room temperature for 30 minutes. The mixture is concentrated under vacuum, made basic by the addition of ammonium hydroxide and extracted with ethyl acetate. The organic solution is dried and concentrated under vacuum, the thus obtained oily residue is dissolved in isopropanol and the solution is acidified with hydrogen chloride saturated isopropanol. Upon filtration 0.2 g of the product indicated in the title are obtained. M.p. 208°–210° C.

PREPARATION XV 2-aminomethyl-6-ethoxycarbonyl-tetraline hydrochloride a) 6-hydroxy-2-tertbutoxycarbonylaminomethyl-tetraline A mixture of 2-aminomethyl-6-hydroxytetraline (Preparation J in EP-A-436,435) (23.7 g, 0.09 mol) dimethylformamide (185 ml) and triethylamine (90 ml) is cooled to 0° C. Di-tertbutyl-dicarbonate (22.5 g, 0.10 mol) is then stirred in and stirring is continued at room temperature for 3 hours. The reaction mixture is poured into water (1 L), 1 and extracted three times with ethyl ether. The organic extracts are combined washed with water, dried and evaporated to dryness yielding a residue which is then purified by chromatography eluting with a mixture cyclohexane:ethyl acetate 7:3. Yield: 23 g. M.p. 114° C.

b) 2-tertbutoxycarbonylaminomethyl-6-trifluoromethanesulfonyloxy-tetraline

This compound, which is prepared by following essentially the procedure described in Preparation I step a) but starting from the compound obtained in step a) above, is directly employed in the next step.

c) 2-tertbutoxycarbonylaminomethyl-6-vinyl-tetraline

The compound is obtained by following the procedure described in Preparation I step b) but starting from the compound obtained in step b) above. M.p. 70° C.

d) 6-formyl-2-tertbutoxycarbonylaminomethyl-tetraline

The compound is prepared by following the procedure described in Preparation I step c) but starting from the compound obtained in step c) above. M.p. 115° C. (isopropyl ether).

e) 1 2-aminomethyl-6-ethoxycarbonyl-tetraline hydrochloride

A solution of 80% NaClO$_2$ (9 g, 0.08 mol) rand NaHPO$_4$ (8 g, 0.067 mol) in water (40 ml) is added to a solution of the compound obtained in step d) above (2.5 g, 0.0086 mol) in tert-butanol (120 ml).

The reaction mixture is stirred at room temperature for 1 hour, brought to pH$\sim$3 by the addition of 1N HCl and extracted with ethyl acetate. The organic phase is dried over sodium sulfate and the solvent is evaporated off. The thus obtained residue is dissolved in absolute ethanol (100 ml) and hydrogen chloride is bubbled into the obtained solution for 30 minutes. The solvent is evaporated off, the residue is dissolved in water, the aqueous solution is made basic by the addition of ammonium hydroxide, filtered and extracted with ethyl acetate. The organic phase is separated, dried and concentrated to dryness. The product obtained in the form of the free base is converted into the corresponding hydrochloride in isopropanol/ethyl ether yielding the compound of the title with m.p. 200° C.

PREPARATION XVI 2-aminomethyl-6-(2-ethoxycarbonyl)ethyl-tetraline hydrochloride a) 6-(2-ethoxycarbonyl)vinyl-2-tertbutoxycarbonylaminomethyl-tetraline The above compound is obtained by following the procedure described in Preparation I step d) but starting from the compound obtained in Preparation XV, step d).

b) 6-(2-ethoxycarbonyl)ethyl-2-tertbutoxycarbonylaminomethyl-tetraline

The compound obtained in step a) above is hydrogenated as described in Preparation II step a) thus affording the above compound with m.p. 77° C.

c) 2-aminomethyl-6-(2-ethoxycarbonyl)ethyl-tetraline hydrochloride

The compound of the title is obtained by following the procedure described in Preparation II step b) but starting from the compound obtained in step b) above. M.p. 210° C.

EXAMPLE 1

N-[(7-ethoxycarbonyl)-1,2,3,4-tetrahydronaphth-2-yl]-2-hydroxy-2-(3-chlorophenyl)ethanamine A mixture of 2-amino-7-(2-ethoxycarbonyl)-tetraline hydrochloride (Preparation III) (0.2 g, 0.92 mmol), dimethylsulfoxide (2 ml) and 3-chlorostyrene oxide (0.21 g, 1.34 mmol) is heated to 80° C. for 24 hours under nitrogen atmosphere. The reaction mixture is then poured into water and extracted with ethyl acetate. The organic phase is washed with water, dried over sodium sulfate and concentrated under vacuum thus affording a dark yellow oily residue which is converted into the corresponding hydrochloride by treatment with gaseous HCl in isopropanol. The obtained product is recovered by filtration and crystallised from a mixture isopropanol/ether 9/1. The compound of the title (0.12 g) is thus obtained with m.p. 199°–201° C. (isopropanol/ethanol 9/1).

EXAMPLE 2

N-[(7-(2-ethoxycarbonyl)ethyl)-1,2,3,4-tetrahydronaphth-2-yl]-2-hydroxy-2-(3-chlorophenyl)ethanamine hydrochloride A mixture of the compound obtained in Preparation II, but in the form of free base (1.2 g, 0.005 mol), dimethylsulfoxide (6 ml) and 3-chlorostyrene oxide (1.17 g, 0.0073 mol) is heated to 80° C. for 16 hours. The reaction mixture is then poured into water and extracted with ethyl acetate. The organic phase is washed with water, dried over sodium sulfate and concentrated under vacuum thus affording a light yellow oily residue which is purified by silica gel column chromatography eluting with ethyl acetate. The obtained product is dissolved in ethyl ether and hydrogen chloride saturated ethanol is then added thereto. The product which precipitates is recovered by filtration yielding 1.07 g of the compound of the title. M.p. 145°–148° C. (ethanol).

EXAMPLES 3-4

The compounds indicated below are prepared by following the procedure described in Example 2 but starting from the compound obtained in Preparation IV and the pure isomers of 3-chlorostyrene oxide:

EXAMPLE 3

N-[(2R) 7-(2-ethoxycarbonyl)ethyl-1,2,3,4-tetrahydronaphth-2-yl]-(2R)-2-hydroxy-2-(3-chlorophenyl)ethanamine hydrochloride M.p. 138°–140° C. (ethyl ether) $[\alpha]_D^{20} = +31.5°$ (c=1%, MeOH).

EXAMPLE 4

N-[(2R) 7-(2-ethoxycarbonyl)ethyl-1,2,3,4-tetrahydronaphth-2-yl]-(2S)-2-hydroxy2-(3-chlorophenyl)ethanamine hydrochloride

EXAMPLES 5-6

The compounds indicated below are prepared by following the procedure described in Example 2 but starting from the compound obtained in Preparation VII and the pure isomers of 3-chlorostyrene oxide:

EXAMPLE 5

N-[(2S) 7-(2-ethoxycarbonyl)ethyl-1,2,3,4-tetrahydronaphth-2-yl]-(2R)-2-hydroxy-2-(3-chlorophenyl)ethanamine hydrochloride M.p. 164°–166° C. (isopropyl ether) $[\alpha]_D^{20} = -78.5°$ (c=1%, MeOH).

EXAMPLE 6

N-[(2S) 7-(2-ethoxycarbonyl)ethyl-1,2,3,4-tetrahydronaphth-2-yl]-(2S)-2-hydroxy-2-(3-chlorophenyl)ethanamine hydrochloride

EXAMPLE 7

N-[7-(2-carboxy)ethyl-1,2,3,4-tetrahydronaphth-2-yl]-2-hydroxy-2-(3-chlorophenyl) ethanamine hydrochloride The compound of Example 2 (450 mg, 1.1 mmol) is dissolved in absolute ethanol (3 ml) and 1N NaOH (2 ml) is added thereto. The mixture is stirred at room temperature for 3–4 hours, the solvent is evaporated off and the residue is dissolved in water, the aqueous solution is washed with ethyl ether and 1N HCl is added to the aqueous phase up to acidic pH. The precipitate is recovered by filtration and dried affording 100 mg of the compound of the title. M.p. 152°–155° C.

I.R. (KBr): 1703 cm$^{-1}$ (—COOH) and 3350 cm$^{-1}$ (—OH). Mass spectrometry: E.I. M+ =411; F.A.B. MH+ =374

EXAMPLE 8

N-[(2S) 7-(2-ethoxycarbonyl)vinyl-1,2,3,4-tetrahydronaphth-2-yl]-(2R)-2-hydroxy-2-(3-chlorophenyl)ethanamine hydrochloride A mixture of the compound obtained in Preparation VI, but in the form of free base, (200 mg, 0.7mmol) and (R)-3-chlorostyrene oxide (152 mg, 0.98 mmol) in ethanol (5 ml) is refluxed for 30 hours. The solvent is evaporated off and the residue is purified by flash chromatography on a silica gel column eluting with a mixture methylene chloride:methanol 9:1. The hydrochloride of the obtained product is prepared in isopropanol yielding 150 mg of the compound of the title.

M.p. 117°–120° C. $[\alpha]_D^{20} = -104°$ (c=0.3%, MeOH).

EXAMPLE 9

N-[(7-(3-ethoxycarbonyl)propyl)-1,2,3,4-tetrahydronaphth-2-yl]-2-hydroxy-2-(3chlorophenyl)ethanamine hydro The compound of the title is prepared by following the procedure described in Example 1 but starting from the compound of Preparation IX step b).

EXAMPLE 10

N-[(2R) 7-(2-ethoxycarbonyl)vinyl-1,2,3,4-tetrahydronaphth-2-yl]-(2R)-2-hydroxy-2-(3-chlorophenyl)ethanamine hydrochloride The compound of the title is prepared by following the procedure described in Example 8 but starting from the compound obtained in Preparation IV step f), in the form of free base and (R)-3-chlorostyrene oxide. M.p. 205°–207° C. $[\alpha]_D^{20} = +56.4°$ (c=0.5% MeOH).

EXAMPLE 11

N-[7(2-ethoxycarbonyl)vinyl-1,2,3,4-tetrahydronaphth-2-yl]-2-hydroxy-2-(3-chloroophenyl)ethanamine hydrochloride The compound of the title is prepared by following the procedure described in Example 8 but starting from the compound obtained in Preparation I step e), as the free base, and 3-chlorostyrene oxide. M.p. 149°–151° C.

EXAMPLE 12

N-[[7-(2-ethoxycarbonyl)vinyl-1,2,3,4-tetrahydronaphth-2-yl]methyl]-2-hydroxy-2-(3-chlorophenyl)ethanamine hydrochloride A mixture of the compound obtained in Preparation XII, as the free base, (0.36 g, 0.0014 mol) and 3-chlorostyrene oxide (0.3 g, 0.0019 mol) in absolute ethanol (20 ml) is refluxed overnight. The solvent is then evaporated off and the residue is purified by chromatography eluting with a mixture ethyl acetate:ethanol 85:15. The hydrochloride of the obtained product is prepared in ethanol affording 0.15 g of the compound of the title. M.p. 217°–219° C.

EXAMPLE 13

N-[[7-(2-ethoxycarbonyl)ethyl-1,2,3,4-tetrahydronaphth-2-yl]methyl]-2-hydroxy-2-(3-chlorophenyl)ethanamine hydrochloride The compound of the title is prepared by following the procedure described in Example 12 but starting from the compound obtained in Preparation XIII. M.p. 177°–179° C.

EXAMPLE 14

N-[(7-ethoxycarbonyl-1,2,3,4-tetrahydronaphth-2-yl)methyl]-2-hydroxy-2-(3-chlorophenyl)ethanamine hydrochloride The compound of the title is prepared by following the procedure described in Example 12 but starting from the compound obtained in Preparation XIV. M.p. 187°–189° C.

EXAMPLE 15

N-[[6-(2-ethoxycarbonyl)ethyl-1,2,3,4-tetrahydronaphth-2-yl]methyl]-2-hydroxy-2(3-chlorophenyl)ethanamine hydrochloride A mixture of the compound obtained in Preparation XVI (2 g, 0.0067 mol) and 3-chlorostyrene oxide (1 g, 0.0065 mol) in absolute ethanol (25 ml) is refluxed overnight. The solvent is then evaporated off, the residue is dissolved in isopropanol and hydrogen chloride is bubbled therein. The precipitate is recovered by filtration affording the compound of the title (1.4 g). M.p. 149° C.

EXAMPLE 16

N-[(6-ethoxycarbonyl-1,2,3,4-tetrahydronaphth-2-yl)methyl]-2-hydroxy-2-(3-chlorophenyl)ethanamine hydrochloride The compound of the title is prepared by following the procedure described in Example 12 but starting from the compound obtained in Preparation XV. M.p. 206° C.

We claim:

1. A compound of formula III

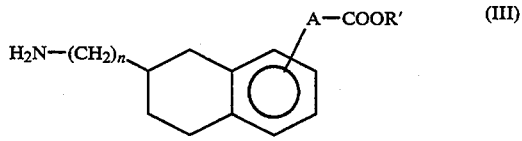

wherein A represents a $C_1$–$C_4$ alkylene or a $C_2$–$C_4$ alkenylene group; R' represents a $C_1$–$C_4$ alkyl group; and n=0; with the proviso that when the —A—COOR' is at position 6 or 7, A cannot represent a methylene group, or a salt or N-protected derivative thereof.

2. A compound according to claim 1 wherein the —A—COOR' group is at position 6 or 7 of the tetraline ring and A represents a $C_2$–$C_3$ alkylene group of a $C_2$ alkenylene group.

3. A compound according to claim 1 wherein A represents a $C_2$–$C_4$ alkylene group.

4. A compound according to claim 2 wherein the —A—COOR' group is at position 6 of the tetraline ring and A represents a $C_2$–$C_3$ alkylene group or a $C_2$ alkenylene group.

5. A compound according to claim 1, wherein A is an ethylene group.

6. A compound according to claim 1, wherein A is an ethylene group at position 6 or 7 of the tetraline ring.

* * * * *